(12) United States Patent
Sanders et al.

(10) Patent No.: US 11,999,986 B2
(45) Date of Patent: *Jun. 4, 2024

(54) PROCESS FOR THE CONVERSION OF LIGNOCELLULOSE MATERIAL INTO AN ORGANIC ACID

(71) Applicant: PURAC BIOCHEM B.V., Gorinchem (NL)

(72) Inventors: Johan Pieter Marinus Sanders, Groningen (NL); Robert Reurd Christophor Bakker, Wageningen (NL)

(73) Assignee: PURAC BIOCHEM B.V., Gorinchem (NL)

( * ) Notice: Subject to any disclaimer, the term of this patent is extended or adjusted under 35 U.S.C. 154(b) by 73 days.

This patent is subject to a terminal disclaimer.

(21) Appl. No.: 17/691,325

(22) Filed: Mar. 10, 2022

(65) Prior Publication Data

US 2022/0195480 A1     Jun. 23, 2022

Related U.S. Application Data

(63) Continuation of application No. 14/353,443, filed as application No. PCT/NL2012/050735 on Oct. 23, 2012, now Pat. No. 11,279,964.

(30) Foreign Application Priority Data

Oct. 25, 2011   (EP) ..................................... 11186513

(51) Int. Cl.
| | |
|---|---|
| C12P 21/06 | (2006.01) |
| C12P 7/46 | (2006.01) |
| C12P 7/54 | (2006.01) |
| C12P 7/56 | (2006.01) |
| C12P 13/04 | (2006.01) |

(52) U.S. Cl.
CPC ................. *C12P 21/06* (2013.01); *C12P 7/46* (2013.01); *C12P 7/54* (2013.01); *C12P 7/56* (2013.01); *C12P 13/04* (2013.01); *Y02P 20/129* (2015.11)

(58) Field of Classification Search
None
See application file for complete search history.

(56) References Cited

U.S. PATENT DOCUMENTS

| | | |
|---|---|---|
| 5,498,766 A | 3/1996 | Stuart et al. |
| 5,508,183 A | 4/1996 | Scott et al. |
| 5,932,455 A | 8/1999 | Viljava et al. |
| 6,623,599 B1 * | 9/2003 | Laurila-Lumme ..... D21H 23/10 162/158 |
| 7,144,977 B2 * | 12/2006 | Eyal ........................ C07C 67/08 562/580 |
| 7,217,545 B2 | 5/2007 | Agblevor et al. |
| 7,705,180 B2 * | 4/2010 | van Krieken ......... C07C 51/412 562/589 |
| 11,279,964 B2 * | 3/2022 | Sanders ..................... C12P 7/56 |
| 2005/0281913 A1 | 12/2005 | van Krieken et al. |

FOREIGN PATENT DOCUMENTS

| | | |
|---|---|---|
| CN | 1735962 A | 2/2006 |
| WO | 98/37050 A1 | 8/1998 |
| WO | WO 1998/037050 * | 8/1998 |
| WO | 2004/063382 A2 | 7/2004 |
| WO | WO 2004/063382 * | 7/2004 |
| WO | 2009/025547 A1 | 2/2009 |
| WO | WO 2009025547 * | 2/2009 |
| WO | 2009/134745 A2 | 11/2009 |
| WO | 2011/002824 A1 | 1/2011 |

OTHER PUBLICATIONS

Mass et al. Appl Microbiol Biotechnol. 2006, 72, 861-868.*
Mass et al. Biotechnology for Biofuels. 2008, 1, pp. 1-13.*
Poykio et al. "Calcium carbonate waste from an integrated pulp and paper mill as a potential liming agent". Environ. Chem. Lett. 2008, 6, pp. 47-51.*
May 19, 2016 Office Action issued in European Application No. 12781177.6.
Jan. 28, 2013 International Search Report issued in International Patent Application No. PCT/NL2012/050735.
Feb. 21, 2012 Extended European Search Report issued in European Patent Application No. 11186513.5.
Maas et al., "Lactic acid production from lime-treated wheat straw by Bacillus coagulans: neutralization of acid by fed-batch addition of alkaline substrate," Applied Microbiology and Biotechnology, 2008, pp. 751-758, vol. 78.
Maas et al., "Pilot-scale conversion of lime-treated wheat straw into bioethanol: quality assessment of bioethanol and valorization of side streams by anaerobic digestion and combustion," Biotechnology for Biofuels, 2008, pp. 1-13, vol. 1.
Maas et al., "Lactic acid production from xylose by the fungus Rhizopus oryzae," Applied Microbiology and Biotechnology, 2006, pp. 861-868, vol. 72.
Fernandes et al., "Effects of thermo-chemical pre-treatment on anaerobic biodegradability and hydrolysis of ignocellulosic biomass," Bioresource Technology, 2009, pp. 2577-2578, vol. 100.
Bakker et al., "Alkaline pretreatment of lignocellulosic biomass for integrated biorefinery applications," Sixth International Conference on Renewable Resources & Biorefineries, 2010, p. 68.
Bakker et al., "Mild alkaline pretreatment of cellulosic feedstocks to enhance biofuel production," European Bioethanol Technology Meeting, 2008, pp. 1, 29.

(Continued)

*Primary Examiner* — Vera Afremova
(74) *Attorney, Agent, or Firm* — Oliff PLC

(57) ABSTRACT

The invention relates to a process for the conversion of lignocellulose into an organic acid including an alkaline pretreatment step and a fermentation step, wherein liquid phase obtained in the fermentation step is recycled to the alkaline pretreatment step and/or the fermentation step. Organic acid is recovered as its magnesium of calcium salt from solid phase obtained in the fermentation step.

14 Claims, 1 Drawing Sheet

(56) References Cited

OTHER PUBLICATIONS

Nov. 17, 2015 Office Action issued in Russian Application No. 2014118361.
Feb. 15, 2016 Office Action issued in Chinese Application No. 201280052491.3.

* cited by examiner

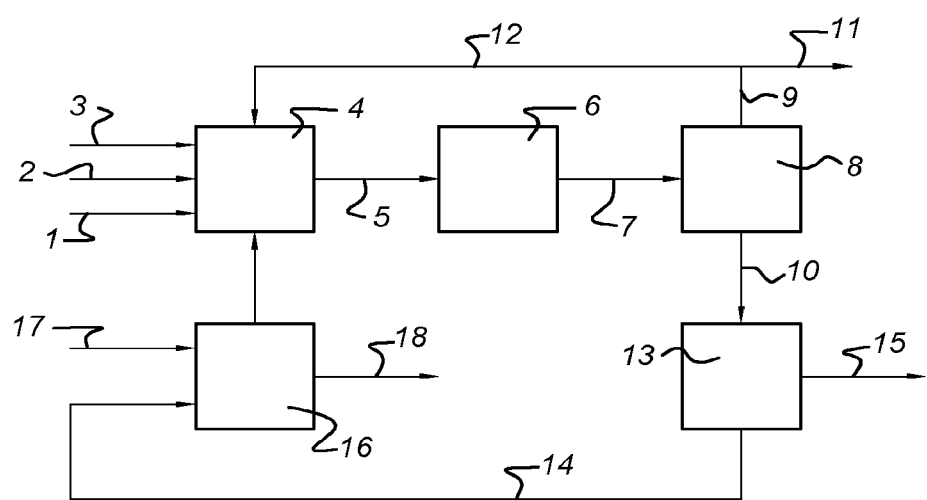

PROCESS FOR THE CONVERSION OF LIGNOCELLULOSE MATERIAL INTO AN ORGANIC ACID

CROSS REFERENCE TO RELATED APPLICATION

This application is a continuation of U.S. application Ser. No. 14/353,443, filed Apr. 22, 2014, the contents of which are incorporated herein by reference.

FIELD OF THE INVENTION

The present invention relates to a process for the conversion of lignocellulose material into an organic acid.

BACKGROUND OF THE INVENTION

It is known to produce organic acids, such as for example lactic acid, succinic acid, or acetic acid by fermentation of biomass that comprises lignocellulose. In WO2009/025547 is for example disclosed a process for the production of lactic acid as a fermentation product from lignocellulosic biomass. In the process of WO2009/025547 lignocellulosic biomass is pretreated with an alkaline agent and then subjected to simultaneous saccharification and fermentation in a fermentor to produce lactic acid or a salt thereof.

A disadvantage of the process of WO2009/025547 is that the fermentation product, i.e. lactic acid or calcium lactate, is recovered in a relatively low concentration. In case the lactic acid recovered would be used for subsequent microbial conversion into ethanol, multiple distillation steps would be needed in order to obtain an ethanol concentration of 96%.

Further, a relatively low yield of the fermentation product will be obtained. In order to obtain sufficient saccharification of the lignocellulose, a relatively severe alkaline pretreatment step, a prehydrolysis step, and/or a relatively high amount of hydrolytic enzyme in the fermentor would be needed.

SUMMARY OF THE INVENTION

It has now been found that if the production of organic acid from lignocellulose material by alkaline pretreatment followed by fermentation of the alkaline pretreated material in a fermentation zone is carried out such that liquid effluent of the fermentation zone is recycled to the alkaline pretreatment step and/or to the fermentation zone, and the organic acid is recovered as magnesium or calcium salt from the solid effluent of the fermentation zone, the organic acid can be obtained in a high concentration, with a high yield and at a high purity.

Accordingly, the invention relates to a process for the conversion of lignocellulose into an organic acid, the process comprising the following steps:
a) pretreating a feed comprising lignocellulose material with an alkaline agent comprising a divalent cation, wherein the divalent cation is a calcium or magnesium cation, in the presence of water at a pretreatment temperature, to obtain an aqueous slurry of alkaline pretreated lignocellulose material;
b) supplying at least part of the slurry of alkaline pretreated lignocellulose material to a fermentation zone and subjecting the pretreated lignocellulose material, in the fermentation zone in the presence of a hydrolytic enzyme and a micro-organism that is able to convert saccharides into an organic acid, to enzymatic hydrolysis and fermentation to obtain a fermentation broth comprising insoluble lignocellulose, precipitated and dissolved salt of the organic acid with the divalent cation, and enzyme;
c) discharging fermentation broth obtained in step (b) from the fermentation zone;
d) separating from the fermentation broth a liquid phase comprising the dissolved salt of the organic acid and a solid phase comprising insoluble lignocellulose and the precipitated salt of the organic acid; and
e) recycling at least part of the liquid phase to alkaline pre-treatment step a) and/or to the fermentation zone.

Since liquid phase is recycled over the fermentation zone, i.e. indirectly via recycling to the alkaline pretreatment step and/or directly, a high conversion per pass of fermentable saccharides into organic acid is not needed in order to obtain a high yield. Unconverted fermentable saccharides will be recycled and can be fermented in a next pass. Therefore, also saccharides that are relatively difficult to ferment, such as for example cellulose oligomers and xylose, can be fermented without the need of a large fermentation zone.

Since part of the hydrolytic enzyme will be recycled with the liquid phase, a relatively low amount of enzyme can be used.

An important advantage of the process according to the invention is that the product, i.e. the organic acid or the calcium or magnesium salt thereof, can be obtained in a relatively high concentration. Due to the recycle, the concentration of dissolved calcium or magnesium salt of the organic acid will accumulate until saturation is achieved. Once saturation is achieved, any further organic acid produced in the fermentation zone will precipitate as its calcium or magnesium salt. Thus, also under process conditions wherein a relatively low amount of organic acid is produced per pass, for example because of a low concentration of lignocellulose and/or of hydrolytic enzyme and/or because of a poor hydrolysis of the lignocellulose material, the product can still be obtained in a desired high yield and concentration. An advantage of producing for example lactic acid in a relatively high concentration is that, if the lactic acid is further converted into other chemicals, e.g. by fermenting the lactic acid into succinic acid or ethanol, such chemicals can also be obtained in a relatively high concentration. In case of the fermentation of lactic acid into ethanol, this implies that less distillation steps are needed to obtain concentrated ethanol.

Also soluble products of the process according to the invention, such as for example amino acids or peptides in case of a protein-containing feed, can be recovered in a sufficiently high concentration since such amino acids or peptides will accumulate in the liquid effluent of the fermentation zone due to the recycle.

A further advantage of the process according to the invention is that it is economically viable to carry it out on a small scale. The process can be operated at atmospheric pressure and is therefore much less capital intensive than known processes for conversion of lignocellulose material. If carried out on a small scale, i.e. by using waste biomass originating from a relatively small area of farm land as lignocellulose material, waste streams from the process according to the invention, such as minerals, lignocellulose residue or calcium carbonate, can be spread out over the farm land from which the lignocellulose material originated in order to increase soil fertility. Thus, transportation costs and costs for concentration of waste streams are avoided.

SUMMARY OF THE DRAWING

In the FIGURE an embodiment of the invention is schematically shown.

DETAILED DESCRIPTION OF THE INVENTION

In the process according to the invention, a feed comprising lignocellulose material is first subjected to an alkaline pretreatment (step a)) and then supplied to a fermentation zone wherein it is subjected to enzymatic hydrolysis and fermentation (step b)). In the fermentation zone, polysaccharides in the lignocellulose material are hydrolysed to obtain fermentable saccharides, which are fermented into one or more organic acids. A fermentation broth is obtained that is discharged from the fermentation zone (step c)) and then separated into a liquid phase and a solid phase (step d)). At least part of the liquid phase is recycled to the alkaline pretreatment step and/or to the fermentation zone (step e)).

The lignocellulose material may be any biomass material comprising lignocellulose. Examples of suitable lignocellulose material are wood, straw, paper, bagasse, grass, or combinations thereof. Preferably, the lignocellulose material is an agricultural waste material such as for example straw or waste paper. The lignocellulose material may be fresh material or dried material. The feed may comprise lignocellulose material that has undergone a pretreatment such as pre-hydrolysis or an extraction step to remove non-fermentable components or to remove components that could inhibit the subsequent hydrolysis and fermentation in step b)).

The lignocellulose material is preferably comminuted material, for example comminuted by cutting, milling, mechanical refining or extrusion in order to improve the accessibility of the material for the alkaline pretreatment and the hydrolysis/fermentation step.

The feed may comprise material other than lignocellulose material, such as domestic waste or industrial residues (e.g. rapeseed press cake, vegetable residue or greenhouse residue). Preferably, the feed comprises at least 30 wt % dry lignocellulose based on the dry weight of organic material in the feed, more preferably at least 50 wt %, even more preferably at least 70 wt %.

In step a), the lignocellulose material is pretreated in order to break open the lignocellulose matrix, to remove lignin, to make lignin more accessible and/or to increase the surface area of the cellulose. As a result of the pretreatment, the lignocellulose material will be more suitable for subsequent hydrolysis and fermentation in step b). Alkaline pretreatment of lignocellulose material is well-known in the art. Any suitable alkaline pretreatment conditions known in the art may be applied in step a).

The feed is pretreated with an alkaline agent comprising a divalent cation, wherein the divalent cation is calcium or magnesium, in the presence of water. The alkaline agent may for example be calcium hydroxide, calcium oxide, magnesium hydroxide, magnesium oxide, or a combination of two or more thereof. Preferably the alkaline agent is calcium hydroxide or calcium oxide, more preferably calcium hydroxide. Typically, the amount of water present is such that the concentration of dry solid lignocellulose is in the range of from 5 to 30 wt % based on the volume of aqueous phase. The amount of alkaline agent is preferably such that a slurry is obtained with a pH in the range of from 8.0 to 14.0, more preferably of from 8.5 to 13.0, even more preferably of from 9.0 to 12.0.

The alkaline pretreatment may be carried out at any suitable pretreatment temperature. Preferably, the pretreatment temperature is in the range of from 20 to 115° C., more preferably of from 50 to 100° C., even more preferably of from 60 to 98° C., still more preferably of from 70 to 95° C.

It will be appreciated that, since the severity of the alkaline pretreatment is not critical in the process according to the invention, the time during which the lignocellulose material is pretreated is not critical either. The material may be pretreated during any suitable time period, for example during a time in the range of from 10 minutes to 100 days, preferably of from 20 minutes to 3 hours, more preferably of from 30 to 60 minutes. It will be appreciated that typically, a lower pretreatment temperature will be combined with a longer pretreatment time.

In step a), an aqueous slurry of alkaline pretreated lignocellulose material is obtained. At least part of the slurry is supplied to a fermentation zone. Preferably, at least 70%, more preferably at least 80 of the slurry will be supplied to the fermentation. Large particles or fibres, preferably particles or fibres with a diameter (particles) or length (fibres) of at least 2 mm are separated from the slurry prior to supplying the slurry to the fermentation zone. Alternatively, for example in case a feed comprising a mixture of different lignocellulose materials with different cellulose contents is used, part of the pretreated lignocellulose material may be separated from the slurry for use in a different process, and the remainder of the slurry will be supplied to the fermentation zone. It may for example be advantageous to separate a pretreated lignocellulose material with a relatively high cellulose content from the slurry in order to use it for paper manufacturing.

The slurry may be subjected to a cooling step or a screening step (for removing large particles or fibres) prior to be supplied to the fermentation zone. In case the pretreatment temperature is higher than the temperature at which the hydrolysis and fermentation are carried out, the alkaline pretreated material is preferably first cooled to the hydrolysis/fermentation temperature.

The slurry comprising pretreated lignocellulose material is supplied to a fermentation zone comprising one or more fermentors in series. The slurry may be batch-wise or continuously supplied to the first fermentor in the fermentation zone.

In the fermentation zone, the pretreated material is subjected, in the presence of a hydrolytic enzyme and a micro-organism that is able to convert saccharides into an organic acid, to enzymatic hydrolysis and fermentation. The hydrolytic enzyme may be any enzyme suitable for the hydrolysis of saccharides in lignocellulose material or combinations of one or more of such enzymes. Such enzymes are known in the art and include cellulase, hemicellulase or combinations thereof, optionally in combination with pectinase or cellobiase. Preferably, at least a cellulase is present as enzyme.

The micro-organism may be any micro-organism or a combination of micro-organisms suitable for converting saccharides into one or more organic acids. Such micro-organisms are known in the art and include bacteria and fungi such as yeast. Preferably, the micro-organism is a lactic acid producing micro-organism, more preferably a lactic acid producing bacterium. Examples of suitable lactic acid producing bacteria are lactobacilli, bifidobacteria, certain Bacillus and Streptococcus species or combinations thereof.

The temperature in the one or more fermentors may be any temperature at which enzymatic hydrolysis and fermentation takes place. Preferably, the temperature is in the range of from 20 to 80° C., more preferably of from 25 to 60° C., even more preferably in the range of from 30 to 50° C. In case the fermentation zone comprises more than one fermentors, the temperature may be different in the different fermentors.

The fermentation may be carried out at any suitable pH, preferably at a pH in the range of from 4.0 to 8.0, more preferably of from 4.5 to 7.5. a pH in the range of from 5.0 to 7.0 is particularly preferred. It will be appreciated that in case the fermentation zone comprises more than one fermentors in series, the pH in a subsequent fermentor will typically be lower than in a preceding fermentor due to additional organic acid formed.

Under the conditions prevailing in the one or more fermentors in the fermentation zone, polysaccharides in the lignocellulose material are first hydrolysed to obtain fermentable saccharides that may include monosaccharides such as glucose, mannose, fructose, mannose, rhamnose, xylose, arabinose, galacturonic acid, disaccharides such as lactose, xylobiose and cellobiose and oligomeric saccharides. The fermentable saccharides are fermented into one or more organic acids by the micro-organism(s) present. It will be appreciated that it will mainly depend on the micro-organism present which organic acid is formed. The organic acid formed as fermentation product may be lactic acid, citric acid, itaconic acid, succinic acid, fumaric acid, glycolic acid, pyruvic acid, acetic acid, glutamic acid, malic acid, propionic acid, butyric acid, gluconic acid and combinations thereof. Preferably, the micro-organism is a lactic acid producing micro-organism, more preferably a lactic acid producing bacterium, and the organic acid formed is lactic acid.

Thus, in the one or more fermentors, a fermentation broth is obtained that comprises insoluble lignocellulose, an organic acid, dissolved salt of the organic acid and the divalent cation, the enzyme, the micro-organism and, once the concentration of dissolved salt of the organic acid has achieved saturation, precipitated salt of the organic acid and the divalent cation. The fermentation broth may comprise non-fermented saccharides.

In case of more than one fermentors in series, typically the entire fermentation broth formed in a fermentor is supplied to the next fermentor in series.

Fermentation broth is discharged from the fermentation zone. In case the fermentation zone comprises more than one fermentors in series, fermentation broth is discharged from the last fermentor in series. The fermentation broth discharged is separated into a liquid phase and a solid phase. Such separation may be done by any suitable means known in the art, such as centrifugation, filtration or sedimentation.

At least part of the liquid phase is recycled to the alkaline pretreatment step and/or to the fermentation zone. Preferably at least 50 vol %, more preferably at least 80 vol %, even more preferably at least 90 vol % and still more preferably at least 95 vol % of the liquid phase is recycled to the alkaline pretreatment step and/or to the fermentation zone. Preferably a small part of the liquid phase, preferably at most 10 vol %, more preferably at most 5 vol % of the liquid phase is removed from the process as a bleed stream.

Preferably, at least part of the liquid phase, more preferably at least 50 vol %, even more preferably at least 80 vol %, is recycled to pretreatment step a). Thus, use is made of the water present in the liquid phase and too much dilution of the dissolved salt of the organic acid in the liquid phase is therewith avoided. It may be advantageous to recycle at least part of the liquid phase directly to the fermentation zone to avoid inactivation of the enzyme that may be present in the recycled liquid phase. In order to strike a balance between undesired dilution and enzyme inactivation, preferably part of the liquid phase is recycled to pretreatment step a) and part directly to the fermentation zone. Preferably at most 50 vol %, more preferably at most 20 vol % of the liquid phase is directly recycled to the fermentation zone.

In case the fermentation zone comprises more than one fermentors, part of the liquid phase may be recycled over a single fermentor or to a preceding fermentor.

The liquid phase comprises dissolved salt of the organic acid and the divalent cation. The liquid phase may further comprise the organic acid, dissolved fermentable saccharides, enzyme, micro-organism and other soluble or solubilised compounds from the lignocellulose material. As a result of the recycle, the dissolved salt of the organic acid will accumulate in the liquid phase until its saturation concentration is reached. Any additional organic acid produced in the fermentation zone will then result in precipitation of the organic acid produced in the form of its calcium or magnesium salt. Thus, after a certain time on stream, a fermentation broth will be obtained that comprises precipitated salt of organic acid. The precipitated salt will be discharged from the fermentation zone with the broth and end up, after separation, in the solid phase. The salt of the organic acid can be recovered from the solid phase by means known in the art, for example by means of solid-liquid extraction.

Because the liquid phase is recycled, it is not necessary to achieve a high conversion of saccharides into organic acid per pass. Once the concentration of dissolved salt of the organic acid has reached its saturation concentration, any organic acid further formed will precipitate as its divalent cation salt. The salt can be recovered from the solid phase in a relatively high concentration. Therefore, parameters that influence the rate of conversion for the hydrolysis and the fermentation in the fermentation zone such as the severity of the alkaline pretreatment, the amount of enzyme or micro-organism, pH and temperature in the fermentor(s), residence time in the fermentor(s), the fermentability of the saccharides and the concentration of alkaline pretreated lignocellulose material, are less critical. The operating window is therefore much wider than in prior art processes for hydrolysis and fermentation of lignocellulose material, such as for example the process as disclosed in WO2009/025547.

Preferably, the fermentation comprises in the range of from one to five fermentors in series, more preferably of from one to three fermentors in series.

In case the fermentation zone comprises more than one fermentors in series, it may be advantageous to apply different process conditions in the different fermentors, for example by applying a different temperature, pH, residence time and/or by using different hydrolytic enzymes. It may for example be advantageous to operate the first fermentor at a temperature higher than the optimum temperature of the micro-organism, preferably at a relatively short residence time, and to operate succeeding fermentors at a lower temperature in order to operate closer to the optimum temperature of the micro-organism and/or to enhance precipitation of the salt of the organic acid.

The solid phase that is separated from the fermentation broth that is discharged from the fermentation zone may be washed in order to remove contaminants such as fermentation inhibitors and/or any dissolved calcium or magnesium salt of the organic acid and fermentable saccharides from the solid phase. Such washing is carried out at a low temperature in order to avoid too much dissolution of the precipitated salt of the organic acid. Preferably, the washing is carried out at a temperature in the range of from 10 to 50° C., more preferably of from 15 to 40° C. Washing at room temperature is particularly preferred. Washed solid phase and wash water is thus obtained. At least part of the wash water can advantageously be recycled to step a) to provide the water in pretreatment step a), or to the fermentation zone. Recycling to step a) is particularly preferred since any fermentation inhibitors present in the wash water will typically be decomposed into non-inhibiting compounds under the conditions prevailing in step a).

The calcium or magnesium salt of the organic acid may be recovered from the solid phase that is separated from the fermentation broth, preferably after washing. Such recovery may for example be carried out by extraction of the solid phase with water at elevated temperature, preferably at a temperature in the range of from 50 to 120° C., more preferably of from 60 to 100° C. Thus, a concentrated solution of the calcium or magnesium salt of the organic acid in water and an extracted solid phase are obtained. The solution may comprise up to 40 wt % salt of the organic acid. The concentrated solution of the salt may be recovered as product. Alternatively, the salt may be recovered as solid product by cooling the solution in order to precipitate the salt and then recovering the precipitated salt as solid product.

The calcium or magnesium salt of the organic acid thus obtained may for example be used as ingredient for a feed composition or as raw material for fermentation processes such as fermentation of the organic acid into ethanol or succinic acid.

It is an advantage of the process according to the present invention that the salt of the organic acid can be obtained in a highly concentrated form and in a relatively pure form. In case the organic acid is lactic acid, relatively low amounts of acetic acid, furfural and other compounds that may act as an inhibitor for the further fermentation of the lactic acid into products like ethanol of succinic acid, are present. In the process according to the invention, such compounds dissolve in the liquid phase and are recycled to the alkaline pretreatment step a) and/or the fermentation zone or are removed from the process with a bleed stream from the liquid phase. In the alkaline pretreatment step, such compounds will typically be decomposed into compounds that do not act as fermentation inhibitors.

In an embodiment of the invention, the feed comprises protein. The feed may for example comprise protein if it contains a protein-containing lignocellulose material. Examples of suitable protein-containing lignocellulose material are agricultural residues such as sugar beet leaves, beet pulp, potato fibres, potato leaves and peels and press cake from oilseed processing, rape seed straw, vegetable agricultural residues, dried distiller's grains with solubles (DDGS), wet distiller's grain or other highly diluted residues from food or biofuel processes, rape meal or sunflower meal from which most protein is extracted. Such protein-containing lignocellulose material may constitute the entire feed, but may also be part of the feed, the feed further comprising another lignocellulose material. An advantage of using a feed that comprises protein is that the adsorption of enzyme, in particular the adsorption of cellulase and beta-glucosidase, on the lignin present in the lignocellulose material will be reduced during fermentation step b). Thus, enzyme costs will be reduced compared to a process using a feed without protein.

Further, in case the feed comprises protein, amino acids and/or peptides may be advantageously recovered as product from the liquid phase. In case the feed stream comprises protein and recovery of amino acids or peptides is desired, the micro-organism is preferably a micro-organism that is able to hydrolyse protein into its amino acids or peptides. More preferably, the micro-organism is a lactic-acid producing bacterium. Amino acids and/or peptides formed in the fermentation zone may be recovered from the liquid phase by means known in the art, for example by evaporation of the liquid phase.

Preferably, the process further comprises a fermentation step wherein the organic acid in the salt of the organic acid that is recovered from the solid phase is fermented into a fermentation product. In case the organic acid is lactic acid, the calcium or magnesium lactate recovered from the solid phase may for example be fermented into succinic acid or ethanol. The fermentation product is then recovered as product by means known in the art. Recovery of ethanol from such fermentation is typically done by means of distillation.

It may be advantageous to add a further acid, i.e. an acid that can be distinguished from the organic acid, during such fermentation step in order to minimize the pH increase due to the conversion of the organic acid. If such further acid is added, a calcium or magnesium salt of the further acid is formed as co-product of the fermentation step. Examples of suitable further acids are sulphuric acid, hydrochloric acid, phosphoric acid.

The extracted solid phase can suitably be used as feed to a power generator. Since the extracted solid phase typically has a low potassium content, slag formation in the power generator is avoided. Most potassium present in the lignocellulose material will typically be discharged from the process with a bleed stream from the liquid phase. Preferably, the extracted solid phase is fed to the power generator as co-feed together with a feed such as for example natural gas, biomass or waste paper. In the power generator, electricity and heat are generated. Preferably, the heat generated is used in step a) to achieve the desired pretreatment temperature.

In an embodiment of the invention, the feed to alkaline pretreatment step a) comprises paper comprising calcium carbonate. In case paper comprising calcium carbonate is used as feed, the extracted solid phase will comprise calcium carbonate. In case such extracted solid phase comprising calcium carbonate is fed to the power generator, calcium oxide will be formed in the power generator. Preferably, such calcium oxide is recycled to alkaline pretreatment step a) as alkaline agent.

As described in more detail hereinabove, in some embodiments of the invention, a magnesium or calcium salt of the further acid is formed in the fermentation of the (salt of the) organic acid recovered from the solid phase. The magnesium or calcium salt of the further acid thus formed may be co-fed to the power generator to form magnesium or calcium oxide. Preferably, such magnesium or calcium oxide is recycled to alkaline pretreatment step a) as alkaline agent.

Alkaline pretreatment step a) is carried out in the presence of water. External water may be directly added to alkaline pretreatment step a). Alternatively, water used in extraction of washing steps in the process according the invention may be recycled to step a). Examples of such water is water that is used to dissolve calcium or magnesium salt of the organic acid from the solid phase obtained in step d), water that is used to wash the extracted solid phase before it is fed to the power generator, or water that is used to wash a high cellulose alkaline pretreated lignocellulose material that is separated from the slurry obtained in step a). Instead of water, aqueous streams that comprise organic material may be used to provide the water in step a), such as for example wet distiller's grain or other streams from food or biofuel processes.

DETAILED DESCRIPTION OF THE DRAWING

In the FIGURE, an embodiment of the invention is schematically shown. Streams of air dry, ground wheat straw 1, calcium hydroxide 2 and water 3 are supplied to container 4 and kept in the container at a pretreatment temperature of 95° C. during 24 hours. After 24 hours, an aqueous slurry of alkaline pretreated straw 5 is discharged from container 4 and supplied to fermentation zone 6 that comprises a single fermentor. Cellulase enzymes, a lactic-acid producing bacterium and nutrients are added to fermentor 6 (not shown). In fermentor 6, the alkaline pretreated lignocellulose material is subjected to enzymatic hydrolysis to form fermentable saccharides. The saccharides thus formed are fermented into lactic acid. Due to the presence of calcium ions in fermentor 6, the lactic acid formed will dissolve as calcium lactate and after the saturation concentration has been reached, calcium lactate precipitates. Fermentation broth 7 comprising insoluble lignocellulose, dissolved and precipitated calcium lactate, and cellulase is discharged from fermentation zone 6 and supplied to separator 8 wherein it is separated into liquid phase 9 and solid phase 10. A small stream 11 of liquid phase is removed from the process as bleed stream. The main part 12 of liquid phase is recycled to container 4, i.e. to the alkaline pretreatment step. Liquid phase 9 comprises dissolved calcium lactate, lactic acid and optionally part of the cellulase and some fermentable saccharides. Solid phase 10 comprises insoluble lignocellulose and precipitated calcium lactate. The solid phase is supplied to solid-liquid extraction unit 13 wherein the solid phase is counter-currently extracted with hot water to obtain extracted solid phase 14 and an aqueous solution of calcium lactate 15. Solution 15 may be recovered as product. Alternatively, solution 15 is cooled (not shown) to precipitate the calcium lactate and solid calcium lactate is recovered as product. Instead of recovering calcium lactate as product, the calcium lactate may be further fermented into ethanol or other fermentation products (not shown).

Extracted solid phase 14 is supplied as co-feed to power generator 16, together with main feed 17 that may for example be natural gas, biomass and/or waste paper. In generator 16, electricity 18 and heat 19 are generated. Heat 19 is used to heat the content of container 4 to the pretreatment temperature of 95° C.

The invention claimed is:

1. A process for the conversion of lignocellulose into an organic acid, the process comprising the following steps:
    a) pretreating a feed comprising lignocellulose material with an alkaline agent comprising a divalent cation, wherein the divalent cation is a calcium or magnesium cation, in the presence of water at a pretreatment temperature, to obtain an aqueous slurry of alkaline pretreated lignocellulose material;
    b) supplying at least part of the slurry of alkaline pretreated lignocellulose material to a fermentation zone and subjecting the pretreated lignocellulose material, in the fermentation zone in the presence of a hydrolytic enzyme and a micro-organism that is able to convert saccharides into an organic acid, to enzymatic hydrolysis and fermentation to obtain a fermentation broth comprising insoluble lignocellulose, precipitated and dissolved salt of the organic acid with the divalent cation, and enzyme;
    c) discharging fermentation broth obtained in step b) from the fermentation zone;
    d) separating from the discharged fermentation broth a liquid phase comprising the dissolved salt of the organic acid and a solid phase comprising insoluble lignocellulose and the precipitated salt of the organic acid, washing the separated solid phase with water at a temperature in the range of from 10 to 50° C. to obtain a washed solid phase and wash water; and supplying at least part of the wash water to step a);
    e) recycling at least part of the liquid phase separated in step d) to said alkaline pre-treatment step a) and/or to the fermentation zone; and,
    f) recovering the salt of the organic acid from the washed solid phase separated in step d) by extracting said washed solid phase with water at a temperature in the range of from 60 to 100° C. to obtain a solution of the salt of the organic acid and an extracted solid phase.

2. The process according to claim 1, wherein at least part of the liquid phase separated in step d) is recycled to step a).

3. The process according to claim 2, wherein at least 50 vol. % of the liquid phase is recycled to step a).

4. The process according to claim 1, wherein the fermentation zone comprises at least two fermentors in series and wherein step c) fermentation broth is discharged from the last fermentor in series.

5. The process according to claim 1, wherein the solid phase separated in step d) is washed with water at a temperature in the range of from 15 to 40° C.

6. The process according to claim 1 further comprising cooling the solution of step f) to obtain precipitated salt of the organic acid and recovering the precipitated salt in solid form.

7. The process according to claim 1 further comprising a fermentation step wherein the salt of organic acid is fermented into a fermentation product and the fermentation product is recovered as product.

8. The process according to claim 7, wherein a further acid which is distinct from said organic acid is added during the fermentation step and a calcium or magnesium salt of the further acid is formed as co-product in the fermentation step.

9. The process according to claim 1, further comprising feeding the extracted solid phase of step f) to a power generator to generate electricity and waste heat.

10. The process according to claim 9, wherein the power generator feed further comprises paper comprising calcium carbonate and wherein calcium oxide is formed in the power generator and further wherein calcium oxide formed in the power generator is recycled to alkaline pretreatment step a) as alkaline agent.

11. The process according to claim 9, wherein the waste heat generated is used to achieve the pretreatment temperature in step a).

12. The process according to claim 1, wherein the micro-organism of step b) is a lactic-acid producing micro-organism and the organic acid is lactic acid.

13. The process according to claim 1, wherein the feed of step a) comprises protein.

14. The process according to claim 13, wherein amino acids and/or peptides are recovered from the liquid phase separated from the fermentation broth.

* * * * *